Figure 1:
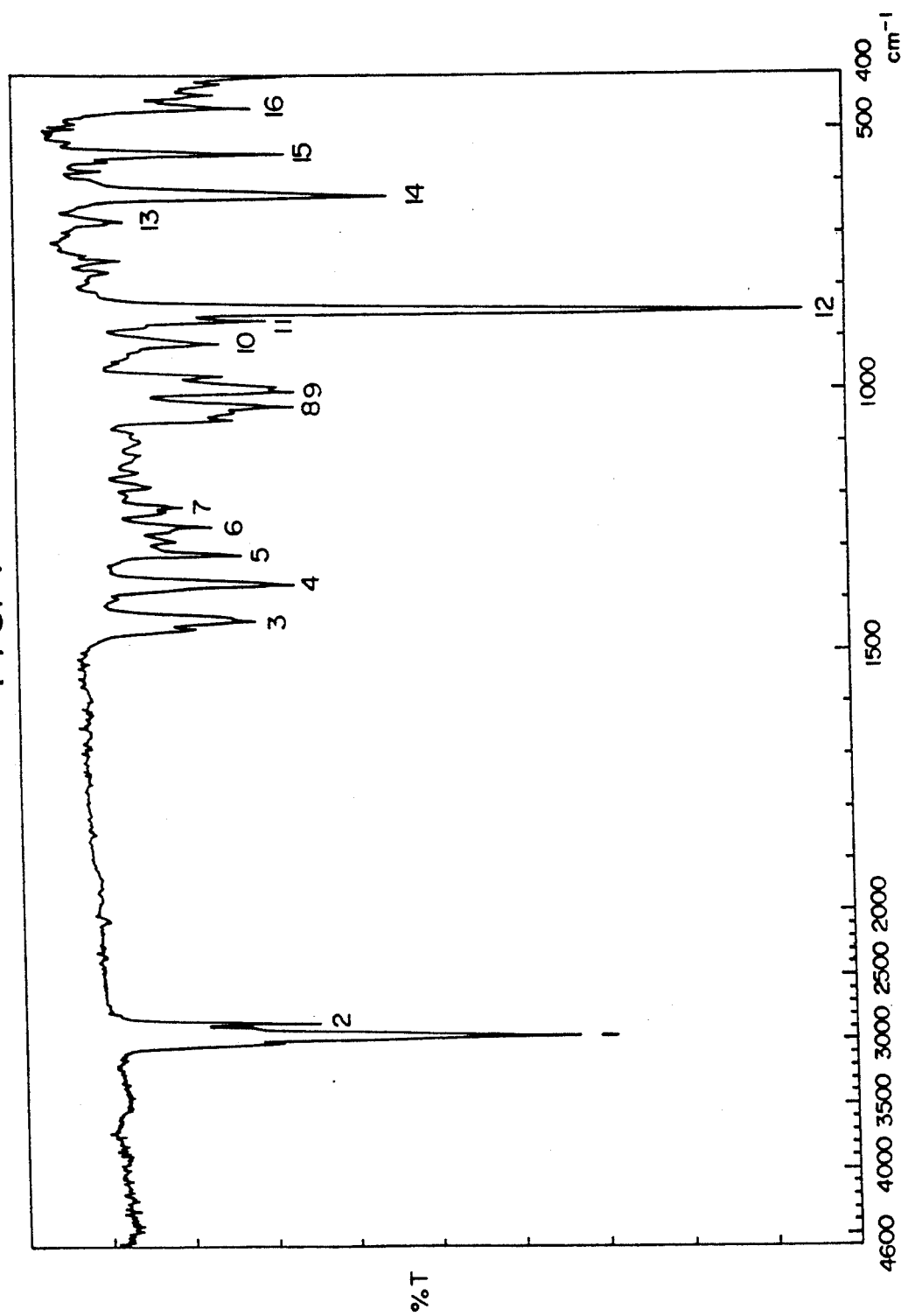
Figure 2:
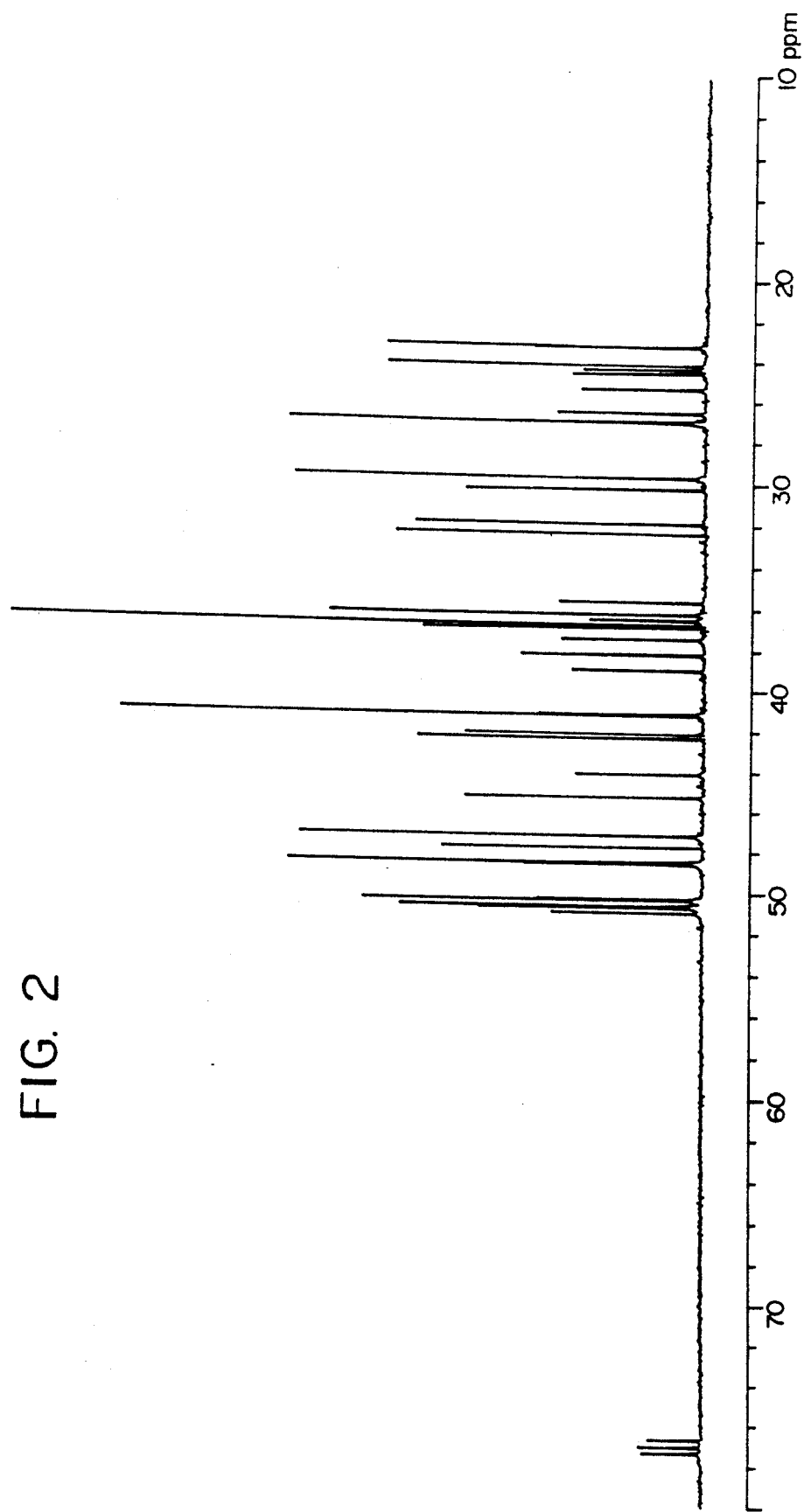

United States Patent [19]

Ikai et al.

[11] Patent Number: 5,153,331

[45] Date of Patent: Oct. 6, 1992

[54] 6-EPITHIOETHYL-3-OXATRICYCLO [3.2.1.0$^{2,4}$] OCTANE AND PROCESS FOR PREPARATION THEREOF

[75] Inventors: Keizo Ikai, Hayama; Masaaki Kobayashi, Yokohama; Keisuke Suzuki, Kawasaki; Mitsuo Matsuno, Yokohama, all of Japan

[73] Assignee: Nippon Oil Company, Ltd., Tokyo, Japan

[21] Appl. No.: 683,174

[22] Filed: Apr. 9, 1991

[30] Foreign Application Priority Data

Apr. 9, 1990 [JP] Japan .................................. 2-92114

[51] Int. Cl.$^5$ .......................................... C07D 409/04
[52] U.S. Cl. ................................ 549/90; 549/1/545
[58] Field of Search ............................ 549/1, 90, 545

[56] References Cited

U.S. PATENT DOCUMENTS

| | | | |
|---|---|---|---|
| 2,094,837 | 10/1937 | Dachlauer | 549/1 |
| 2,094,914 | 10/1937 | Dachlauer | 549/1 |
| 3,183,249 | 5/1965 | Wiese | 549/545 |
| 3,992,420 | 11/1976 | Lind et al. | 549/90 |
| 4,233,131 | 11/1980 | Ratcliffe et al. | 549/90 |

OTHER PUBLICATIONS

M. Sander, Chem. Rev., "Thiiranes," 66, pp. 297-339 (1966).
Chemical Abstracts, vol. 90, 1979, Columbus, Ohio, US; abstract No. 22696s, Kassyan L.: "Synthesis of cyclic diepoxides".
Chemical Abstracts, vol. 95, No. 36, 1981, Columbus, Ohio, US; abstract No. 133908k, Lozinskii M. O.: "Polymeric composition" p. 41: abstract SU-A-836 040 (Dnepropetrovsk State University) May 7, 1981.

Primary Examiner—Glennon H. Hollrah
Assistant Examiner—Mark W. Russell
Attorney, Agent, or Firm—Wenderoth, Lind & Ponack

[57] ABSTRACT

6-Epithioethyl-3-oxatricyclo [3.2.1.0$^{2,4}$] octane, a novel compound, is prepared by reaction of the corresponding 6-epoxyethyl-3-oxatricyclo [3.2.1.0$^{2,4}$] octane with an ammonium or alkali or alkaline earth metal thiocyanate or a thiourea, and useful as a monomer for preparations of, e.g., heat resistant plastics and plastics for optical use.

2 Claims, 2 Drawing Sheets

6-EPITHIOETHYL-3-OXATRICYCLO [3.2.1.0$^{2,4}$] OCTANE AND PROCESS FOR PREPARATION THEREOF

INDUSTRIALLY APPLICABLE FIELD

This invention relates to a novel compound 6-epithioethyl-3-oxatricyclo [3.2.1.0$^{2,4}$] octane and a process for preparation thereof.

PRIOR ART AND PROBLEMS TO BE SOLVED BY THE INVENTION

Although 6-epoxyethyl-3-oxatricyclo [3.2.1.0$^{2,4}$ octane is a known compound [L. I. Kasyan, M. F. Bombushkary, M. S. Malinobsky et al., Ukr. Knim. Zh., 44, 956 (1978)], a compound is not known which has an episulfido group in place of the epoxy group therein. By ring-opening polymerization of 6-epithioethyl-3-oxactricyclo [3.2.1.0$^{2,4}$] octane, a polysulfide having a bicyclo [2.2.1] heptane skeleton can be obtained. Since this polymer has a bicyclo [2.2.1]heptane skeleton and contains sulfur, it is expected to be amorphous and have a high glass transition temperature and exhibit a large refractive index and a low dispersibility. Such a polymer can be utilized as a heat resistant plastic or a plastic for optical use. Thus the present inventors devoted themselves to studies, and as a result they formed a process for efficient synthesis of 6-epithioethyl-3-oxatricyclo [3.2.1.0$^{2,4}$] octane, promising as a raw monomer of heat resistant plastics and plastics for optical use, from 6-epoxyethyl-3-oxatricyclo [3.2.1.0$^{2,4}$] and completed the invention.

OBJECTS OF THE INVENTION

An object of this invention is to provide a novel compound 6-epithioethyl-3-oxatricyclo [3.2.1.9$^{2,4}$] octane.

Another object of the invention is to provide a process for preparation of this novel compound 6-epithioethyl-3-oxatricyclo [3.2.1.0$^{2,4}$] octane.

MEANS FOR SOLVING THE PROBLEMS

Namely, the invention contains two inventions, and its specified invention is 6-epithioethyl-3-oxatricyclo [3.2.1.9$^{2,4}$] octane.

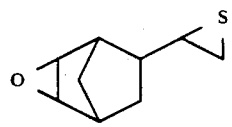

(I)

Further, the second invention of this invention is a process for preparation of (I) which comprises reacting a 6-epoxyethyl-3-oxatricyclo 3.2.1.0$^{2,4}$] octane

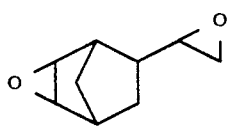

(II)

with a thiocyanate represented by the general formula $$M(SCN)_n \qquad (III)$$

wherein M is a monovalent or divalent metal ion, $NH_4$ or a primary to quaternary ammonium ion having an alkyl group having 1 to 4 carbon atoms, and n is an integer of 1 or 2, and/or a thiourea represented by the general formula $$(R_2N)_2C = S \qquad (IV)$$

wherein R is hydrogen, an alkyl group having 1 to 10 carbon atoms or an aryl group, in the presence or absence of a solvent. 6-epithioethyl-3-oxatricyclo [3.2.1.0$^{2,4}$] octane (I) of the invention is a novel compound. The reaction to convert an epoxy group to an episulfido group is known in a literature [M. Sander, Chem. Rev., 66, 297 (1966)]. However, any example has not yet been known wherein this reaction was carried out on the compound of (II). Conduction of this reaction on the compound of (II) revealed that the 6-epoxyethyl group alone among the two epoxy groups in (II) is converted to an episulfido group and becomes 6-episulfidoethyl. This chemical reaction equation is shown below.

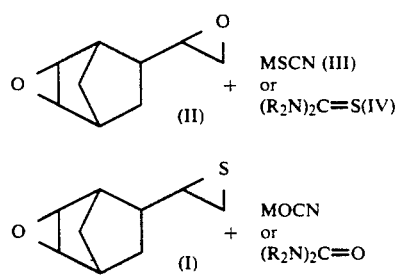

Now, referring to the accompanying drawings, FIG. 1 is an IR chart of 6- epithioethyl-3-oxatricyclo [3.2.1.0$^{2,4}$] octane. FIG. 3 is a $^{13}C$ NMR chart of the above compound.

Although in (II), a raw material, there exist in total four stereoisomers, namely two endo-6-epoxy isomers and two exo-6-epoxy isomers, it is ascertained by $^{13}C$ NMR that four stereoisomers exist likewise in (I). Namely, 36 carbons having different environments should exist in a mixture of the four stereisomers and thus it is anticipated that 36 signals are observed in its NMR spectrum, and in fact 35 signals are observed. The residual one signal is considered to overlap with another signal. These four isomeric structures are Ia to Id shown in the following formulae, which is also similar with (II).

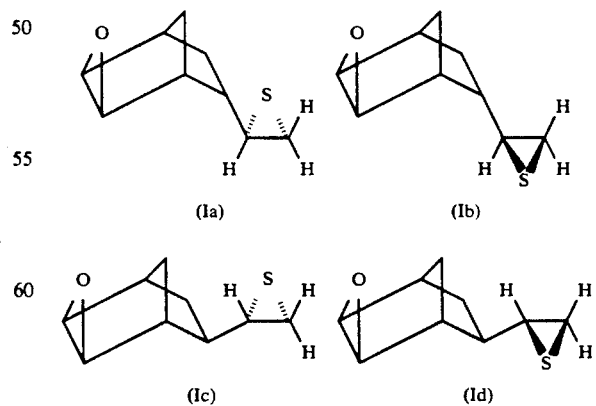

Although 6-epithioethyl-3-oxatricyclo [3.2.1.0$^{2,4}$] octane (I) of the invention can be prepared according to any preparation process, (I) is usually prepared by reacting 6-epoxyethyl-3-oxatricyclo [3.2.1.0$^{2.4}$] octane (II) with a thiocyanate represented by the general formula

M(SCN)$_n$  (III)

wherein M is a monovalent or divalent metal ion, NH$_4$ or a primary to quaternary ammonium ion having an alkyl group having 1 to 4 carbon atoms, and n is an integer of 1 or 2, and/or a thiourea represented by the general formula

(R$_2$N)$_2$C=S  (IV)

wherein R is hydrogen, an alkyl group having 1 to 10 carbon atoms or an aryl group, in the presence or absence of a solvent.

Specific examples of thiocyanates (III) to be used in the invention are metal salts such as sodium thiocyanate, potassium thiocyanate, magnesium thiocyanate, calcium thiocyanate, zinc thiocyanate and copper thiocyanate; ammonium salts such as ammonium thiocyanate, monomethylammonium thiocyanate, monoethylammonium thiocyanate, monopropylammonium thiocyanate, monobutylammonium thiocyanate, dimethylammonium thiocyanate, diethylammonium thiocyanate, dipropylammonium thiocyanate, dibutylammonium thiocyanate, trimethylammnoium thiocyanate, triethylammonium thiocyanate, tripropylammonium thiocyanate, tributylammonium thiocyanate, tetramethylammonium thiocyanate, tetraethylammonium thiocyanate, tetrapropylammonium thiocyanate and tetrabutylammonium thiocyanate; etc. Further, specific examples of thioureas (IV) are thiourea, N-methylthiourea, N-ethylthiourea, N-propylthiourea, N-butylthiourea, N-hexylthiourea, N-cyclohexylthiourea, N-phenylthiourea, N-octylthiourea, N-decylthiourea, N,N-dimethylthiourea, N,N-diethylthiourea, N,N-dibutylthiourea, N,N-dihexylthiourea, N,N-dicyclohexylthiourea, N,N-diphenylthiourea, N,N'-dimethylthiourea, N,N'-diethylthiourea, N,N'-dibutylthiourea N,N'-dihexylthiourea, N,N'-dicyclohexylthiourea, N,N'-diphenylthiourea, N-ethyl-N-methylthiourea, N-butyl-N-methylthiourea, N-hexyl-N-methylthiourea, N-methyl-N-phenylthiourea, N-butyl-N-ethylthiourea, N-ethyl-N-hexylthiourea, N-ethyl-N-phenylthiourea, N-ethyl-N'-methylthiourea, N-butyl-N'-methylthiourea, N-hexyl-N'-methylthiourea, N-methyl-N'-phenylthiourea, N-butyl-N'-ethylthiourea, N-ethyl-N'-hexylthiourea, N-ethyl-N'-phenylthiourea, N,N,N'-trimethylthiourea, N,N,N'-triethylthiourea, N,N,N'-tributylthiourea, N,N,N'-trihexylthiourea, N,N,N'-tricyclohexylthiourea, N-N,N'-triphenylthiourea, N,N-diethyl-N'-methylthiourea, N,N-dibutyl-N'-methylthiourea, N,N-dihexyl-N'-methylthiourea, N,N-dimethyl-N'-phenylthiourea, N,N,N',N'-tetramethylthiourea, N,N,N',N'-tetraethylthiourea, N,N,N',N'-tetrabutylthiourea, N,N,N',N'-tetraphenylthiourea, N,N,N'-triethyl-N'-methylthiourea, N,N,N'-tripropyl-N'-methylthiourea, N,N,N'-tributyl-N'-methylthiourea, N,N,N'-trihexyl-N'-methylthiourea, N,N,N'-tricyclohexyl-N'-methylthiourea, N-butyl-N,N',N'-trimethylthiourea, N,N,N'-trimethyl-N'-phenylthiourea, N,N',N'-trimethylthiourea, N,N-diethyl-N',N'-dimethylthiourea, N,N-dibutyl-N',N'-dimethylthiourea, N-dihexyl-N,N'-dimethylthiourea, N,N-dimethyl-N',N'-diphenylthiourea, etc. These may be used in combination of two or more, or a thiocyanate (III) and a thiourea (IV) may be used together. The molar ratio of a thiocyanate (III) and/or a thiourea (IV) to (II) is suitably 1 to 2.

It is not necessary to use a solvent, but preferably there is used water, an alcohol having 1 to 5 carbon atoms or an ether having 4 to 6 carbon atoms and 1 to 3 oxygen atoms or a mixed solvent thereof. Specific examples thereof include water, alcoholic solvents such as methanol, ethanol, propanol, butanol, ethylene glycol, ethylene glycol monomethyl ether, ethylene glycol monoethyl ether and ethylene glycol monopropyl ether; etheric solvents such as diethyl ether, diisoproply ether, tetrahydrofuran, dioxane, ethylene glycol diethyl ether, ethylene glycol ethyl methyl ether and diethylene glycol dimethyl ether; etc.

In reaction of (II) with (III) and/or (IV) there can be adopted, as a method for their mixing, besides usual mechanical stirring mechanochemical mixing by a ball mill or the like, or sonochemical mixing by ultrasonic irradiation.

The reaction temperature is usually 0 to 100° C., preferably 10 to 50° C., and the reaction time is usually 3 to 20 hours, preferably 4 to 10 hours.

After completion of the reaction, the solvent is distilled away, post treatment is carried out in a conventional manner and the resulting organic layer is separated and purified to obtain the desired 6-epithioethyl-3-oxatricyclo [3.2.1.0$^{2.4}$] octane (I).

This invention provides a novel compound 6-epithioethyl-3-oxatricyclo [3.2.1.0$^{2.4}$] octane promising as a raw monomer of heat resistant plastics and plastics for optical use and its preparation method.

The invention is further specifically described below according to examples, but not limited at all by these examples.

EXAMPLE 1

6-Epoxyethyl-3-oxatricyclo [3.2.1.0 $^{2.4}$] octane (42g, 0.28mol), ammonium thiocyanate (23g, 0.30 mol) and tetrahydrofuran (125 ml) were placed in a 200-ml eggplant type flask, and stirred with a magnetic stirrer in a water bath of 50° C. Although first the reaction solution was completely uniform, a white precipitate was deposited about 30 minutes later. 5 hours later, the reaction mixture was suction filtered by a Nutsche to remove the white precipitate, and the filtrate was concentrated by a rotary evaporator. Toluene (250 ml) and water (80 ml) were added to the concentrate, and after separation of the water layer the toluene layer was washed (80 ml ×2). The toluene layer was dried over magnesium sulfate and the toluene was then distilled away by a rotary evaporator. The concentrate was simply distillated under reduced pressure to obtain 6-epithioethyl-3-oxatricyclo [3.2.1,0$^{2.4}$] octane (40g, yield 87%). Colorless oil; b.p. 90–93° C./2mmHg; n$_D$ 1.5294; IR (neat) 3030(m), 2968(s), 1446(m), 1375(m), 1319(m), 1035(m), 1007(m), 849(s) cm$^{-1}$; $^{13}$C NMR(CDCl$_3$) δ23.1, 23.3, 24.1, 24.3, 24.5, 25.3, 26.5, 26.9, 29.7, 30.2, 31.9, 32.3 (CH$_2$); 35.6, 36.2, 36.5, 36.7, 36.9, 37.4, 38.2, 39.0, 41.1, 41.2, 42.1, 42.3, 44.1, 45.3, 47.2, 47.7, 48.5, 48.6, 50.2, 50.4, 50.6, 50.7, 51.0(CH).

| Experimental analysis (as C$_9$H$_{12}$OS) | | | | |
|---|---|---|---|---|
| | (C %) | H(%) | O(%) | S(%) |
| Found | 64.9 | 7.4 | 9.3 | 18.9 |
| Calculated | 64.3 | 7.2 | 9.5 | 19.1 |

EXAMPLE 2

Reaction was carried out in the same manner as in Example 1 using 6-epoxyethyl-3-oxatricyclo [3.2.1.0$^4$] octane (20g, 0.13 mol), thiourea (11g, 0.14 mol) and diglyme (200 ml) to obtain 6-epithioethyl-3-oxatricyclo [3.2.1.0²·⁴] octane (18g, yield 81%).

What we claim is:

1. 6-Epithioethyl-3-oxatricyclo [3.2.1.0²·⁴] octane

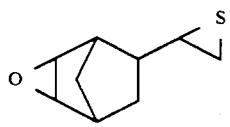
(I)

2. A process for preparation of 6-epithioethyl-3-oxatricyclo [3.2.1.0²·⁴] octane which comprises reacting 6-epoxyethyl-3-oxatricyclo [3.2.1.0²·⁴] octane

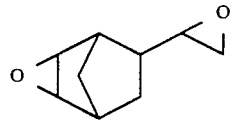
(II)

with a thiocyanate represented by the general formula $$M(SCN)_n \quad \text{(III)}$$

wherein M is a monovalent or divalent metal ion, $NH_4$ or a primary to quaternary ammonium ion having an alkyl group having 1 to 4 carbon atoms, and n is an integer of 1 or 2, and/or a thiourea represented by the general formula $$(R_2N)_2C=S \quad \text{(IV)}$$

wherein R is hydrogen, an alkyl group having 1 to 10 carbon atoms or an aryl group, in the presence or absence of a solvent.

* * * * *